(12) United States Patent
Selic

(10) Patent No.: US 8,212,051 B2
(45) Date of Patent: Jul. 3, 2012

(54) PROCESS FOR THE PREPARATION OF PURE IRBESARTAN

(75) Inventor: Lovro Selic, Celje (SI)

(73) Assignee: Lek Pharmaceuticals, D.D., Ljubljana (SI)

( * ) Notice: Subject to any disclaimer, the term of this patent is extended or adjusted under 35 U.S.C. 154(b) by 337 days.

(21) Appl. No.: 12/299,880

(22) PCT Filed: Apr. 4, 2007

(86) PCT No.: PCT/EP2007/053283
§ 371 (c)(1),
(2), (4) Date: Mar. 13, 2009

(87) PCT Pub. No.: WO2007/115990
PCT Pub. Date: Oct. 18, 2007

(65) Prior Publication Data
US 2009/0240060 A1    Sep. 24, 2009

(30) Foreign Application Priority Data

Apr. 7, 2006 (EP) .................................. 06007375

(51) Int. Cl.
*A61K 31/4184* (2006.01)
*C07D 403/10* (2006.01)
(52) U.S. Cl. ....................... 548/253; 514/381
(58) Field of Classification Search ............... 48/253; 548/253; 514/381
See application file for complete search history.

(56) References Cited

U.S. PATENT DOCUMENTS

| 5,270,317 A | 12/1993 | Bernhart et al. |
| 5,352,788 A * | 10/1994 | Bernhart et al. ............. 544/319 |
| 5,541,209 A | 7/1996 | Spinale |

FOREIGN PATENT DOCUMENTS

| JP | 5-222041 A | 8/1993 |
| WO | WO 99/38847 A1 | 8/1999 |
| WO | WO 9938847 A1 * | 8/1999 |
| WO | WO 2004/007482 A2 | 1/2004 |
| WO | WO 2004/065383 A2 | 8/2004 |
| WO | WO 2005/051928 A1 | 6/2005 |
| WO | WO 2006/011859 A2 | 2/2006 |
| WO | WO 2006011859 A2 * | 2/2006 |
| WO | WO 2006/046043 A1 | 5/2006 |

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*

* cited by examiner

*Primary Examiner* — Joseph Kosack
*Assistant Examiner* — Matthew Coughlin
(74) *Attorney, Agent, or Firm* — Arent Fox LLP

(57) ABSTRACT

A process for the manufacturing of a pure irbesartan comprising converting irbesartan or a protected derivative thereof into an isolated hydrohalide acid addition salt, whereupon said hydrohalide acid addition salt is converted into the irbesartan is described.

25 Claims, 2 Drawing Sheets

PROCESS FOR THE PREPARATION OF PURE IRBESARTAN

CROSS-REFERENCE TO RELATED APPLICATION

This application is a National Stage entry of International Application No. PCT/EP2007/053283, filed Apr. 4, 2007, which claims priority to European Patent Application No. 06007375.6 filed Apr. 7, 2006, the entire specification claims and drawings of which are incorporated herein by reference.

FIELD OF THE INVENTION

The invention belongs to the field of organic chemistry and relates to a novel synthetic process for the preparation of pure irbesartan, preferably exceeding 99.7% as determined by HPLC. The purity of active pharmaceutical ingredient is of utmost importance in pharmaceutical technology

BACKGROUND OF THE INVENTION

Irbesartan, which is chemically 2-n-butyl-3-[[2'-(tetrazol-5-yl)biphenyl-4-yl]methyl]-1.3-diazaspiro[4.4]non-1-en-4-one (3) is an antagonist of angiotensin-II receptors and acts as an antihypertensic. The compound prepared according to U.S. Pat. No. 5,270,317 is polymorph A and crystallizes in the habit of stable and non-hygroscopic needles, which can be stored and incorporated into pharmaceutical formulations without any decomposition. During the synthesis it is convenient to prepare irbesartan from its protected derivative, e.g. from 2-butyl-3-[[2'-[1-(triphenylmethyl)-1H-tetrazol-5-yl][1,1'-biphenyl]-4-yl]methyl]-1,3-diazaspiro[4.4]non-1-en-4-one (1). The deprotection reaction normally results in a mixture or irbesartan and triphenylmethanole or other compound formed from protecting group that both exhibit similar solubilities in variety of solvents and are thus hard to separate by conventional means.

An approach, known for deprotection of structurally similar trityl losartan, to prepare a potassium salt, which could be separated due its solubility in aqueous media, is not feasible, because an attempt to convert irbesartan to potassium salt by KOH results in degradation, to which the spiro system of irbesartan is sensitive in alkaline media.

None of the disclosures of preparation of irbesartan address the purification thereof via hydrohalide acid addition salts. Thus WO 04/007482 teaches the acidification to pH 2-3.5 of trityl irbesartan, which is sufficient to remove the protecting group, but not to convert into an acid addition salt; WO 04/065383 is likewise silent on hydrohalide acid addition salts. WO 06/011859 relates to the preparation of a hydrochloride salt of irbesartan in order to incorporate it into a pharmaceutical formulation. WO99/38847 mentions optional conversion of irbesartan into hydrochloride, hydrobromide or hydrogen sulfate salts. No specific hydrobromide salt of irbesartan has however yet been isolated nor any advantage of any specific crystalline hydrobromide salt has been postulated.

DISCLOSURE OF THE INVENTION

Our invention is in one aspect a process comprising following steps:
  converting protected irbesartan into hydrohalide salt of irbesartan; in particular hydrobromide or hydrochloride; more particular hydrobromide salt, even more particular crystalline hydrobromide salt;
  isolating said salt of irbesartan; and
  converting said isolated salt of irbesartan into irbesartan.

This is in more specific aspect a process for the manufacturing of a pure irbesartan characterized in that irbesartan or a protected derivative thereof is converted into an isolated hydrohalide acid addition salt; in particular into hydrobromide, particularly into crystalline hydrobromide; whereupon said hydrohalide acid addition salt is converted into the irbesartan, even more specifically where the purity of irbesartan is above 99.6%, preferably above 99.8% as measured by HPLC Aspect of the invention is in detail a process for the purification of the 2-n-butyl-3-[[2'-(tetrazol-5-yl)biphenyl-4-yl]methyl]-1.3-diazaspiro[4.4]non-1-en-4-one characterized in that the 2-n-butyl-3-[[2'-(tetrazol-5-yl)biphenyl-4-yl]methyl]-1,3-diazaspiro[4.4]non-1-en-4-one or a protected derivative thereof is converted into an isolated hydrohalide acid addition salt whereupon said hydrohalide acid addition salt is converted into the 2-n-butyl-3-[[2'-(tetrazol-5-yl)biphenyl-4-yl]methyl]-1.3-diazaspiro[4.4]non-1-en-4-one.

More specific aspect of the invention is a process for synthesis of 2-n-butyl-3-[[2'-(tetrazol-5-yl)biphenyl-4-yl]methyl]-1,3-diazaspiro[4.4]non-1-en-4-one characterized by that it comprises following steps:
  providing a solution or suspension of 2-n-butyl-3-[[2'-(trityl tetrazol-5-yl)biphenyl-4-yl]methyl]-1.3-diazaspiro[4.4]non-1-en-4-one in a mixture of an organic solvent miscible with water and water;
  adding hydrohalide thereto until pH is between 0 and 3;
  isolating 2-n-butyl-3-[[2'-(tetrazol-5-yl)biphenyl-4-yl]methyl]-1.3-diazaspiro[4.4]non-1-en-4-one hydrohalide in solid form;
  (optionally) recrystallizing said 2-n-butyl-3-[[2'-(tetrazol-5-yl)biphenyl-4-yl]methyl]-1.3-diazaspiro[4.4]non-1-en-4-one hydrohalide
  dissolving obtained 2-n-butyl-3-[[2'-(tetrazol-5-yl)biphenyl-4-yl]methyl]-1.3-diazaspiro[4.4]non-1-en-4-one hydrohalide in a mixture of an organic solvent miscible with water and water;
  adding an aqueous solution of a base thereto; and
  isolating 2-n-butyl-3-[[2'-(tetrazol-5-yl)biphenyl-4-yl]methyl]-1.3-diazaspiro[4.4]non-1-en-4-one in solid form; or
  extracting 2-n-butyl-3-[[2'-(tetrazol-5-yl)biphenyl-4-yl]methyl]-1.3-diazaspiro[4.4]non-1-en-4-one with the solvent nonmiscible with water; and
  isolating 2-n-butyl-3-[[2'-(tetrazol-5-yl)biphenyl-4-yl]methyl]-1.3-diazaspiro[4.4]non-1-en-4-one in solid form by removal of solvent or addition of an antisolvent which mixes with said solvent nonmiscible with water;
where trityl protecting group may be optionally also any other commonly used protecting group.

Addition of hydrohalide (in particular HBr) is in specific embodiment added until pH is between 0 and 2, more specifically between 0.5 and 1.9 to assure complete salt formation. In specific embodiment the isolated hydrobromide salt is crystalline. If the crystalline salt is not formed initially it is an aspect that it is crystallized from suitable solvent, in particular from acetone.

In particular aspect of the inventions crystallization of irbesartan hydrobromide is performed in boiling acetone, more particular at concentration above 120 mg/ml, however alternatively in another aspect at room temperature.

Another aspect of the invention is a process for converting 2-n-butyl-3-[[2'-(tetrazol-5-yl)biphenyl-4-yl]methyl]-1.3-diazaspiro[4.4]non-1-en-4-one hydrohalide, having purity below 90% as measured by HPLC, into 2-n-butyl-3-[[2'-(tetrazol-5-yl)biphenyl-4-yl]methyl]-1.3-diazaspiro[4.4]non-1- en-4-one having purity above 99% as measured by HPLC, characterized by comprising steps:

crystallizing 2-n-butyl-3-[[2'-(tetrazol-5-yl)biphenyl-4-yl]methyl]-1.3-diazaspiro[4.4]non-1-en-4-one hydrohalide from acetone;

dissolving said 2-n-butyl-3-[[2'-(tetrazol-5-yl)biphenyl-4-yl]methyl]-1.3-diazaspiro[4.4]non-1-en-4-one hydrohalide in a mixture of an alcohol and water wherein the ratio of alcohol to water is between 3 and 1;

adding an aqueous solution of an organic or inorganic base thereto in amount sufficient to yield 2-n-butyl-3-[[2'-(tetrazol-5-yl)biphenyl-4-yl]methyl]-1.3-diazaspiro[4.4]non-1-en-4-one; and extracting 2-n-butyl-3-[[2'-(tetrazol-5-yl)biphenyl-4-yl]methyl]-1.3-diazaspiro[4.4]non-1-en-4-one with solvent nonmiscible with water; and isolating 2-n-butyl-3-[[2'-(tetrazol-5-yl)biphenyl-4-yl]methyl]-1.3-diazaspiro[4.4]non-1-en-4-one in solid form by removal of solvent or addition of an antisolvent which mixes with said solvent nonmiscible with water.

In the aspects above a solvent nonmiscible with water is preferably selected from $CH_2Cl_2$, $CCl_4$, $CHCL_3$, most preferably methylene chloride, organic solvent miscible with water is selected from alcohols, carboxylic acids, acetonitrile, acetone, dimethylsulphoxide, N,N-dimethylformamide, N,N-dimethylacetamide, 1,4-dioxane, THF, acetone, preferably from C1-C5 alcohols, most preferably an alcohol is ethanole and base is selected carbonates, hydrogen carbonates, hydroxides, alkoxydes, preferably hydrogen carbonates.

Use of the hydrohalide acid addition salt of 2-n-butyl-3-[[2'-(tetrazol-5-yl)biphenyl-4-yl]methyl]-1.3-diazaspiro[4.4]non-1-en-4-one in the process for manufacturing of 2-n-butyl-3-[[2'-(tetrazol-5-yl)biphenyl-4-yl]methyl]-1.3-diazaspiro[4.4]non-1-en-4-one is also contemplated within the scope of the invention. More particularly the invention relates to the use of hydrobromide, particularly crystalline hydrobromide, more particularly use of specific new forms A or B (which are described below).

The invention specifically provides for new compound: hydrobromide acid addition salt of 2-n-butyl-3-[[2'-(tetrazol-5-yl)biphenyl-4-yl]methyl]-1.3-diazaspiro[4.4]non-1-en-4-one. As this compound exists in various polymorphs, the invention specifically provides for the form containing from 0 to 10% by weight of water, that is from 1 to 1.5 molecule of water per molecule of irbesartan (in specific aspect irbesartan hydrobromide monohydrate); and for the crystalline irbesartan hydrobromide, preferably characterized by diffractions in X-ray diffraction pattern at following 2-theta values: 7.2, 8.1, 11.6, 12.2, 12.7, 13.2, 19.8, 21.9, 22.9 and/or IR spectra having characterizing peaks at 3425, 2964, 2715, 1775, 1628, 1516, 1476, 1328, 1069, 755 $cm^{-1}$; and/and or melting point 196-199° C.

Within the scope of the invention are however contemplated all polymorphs of irbesartan hydrobromide, in particular anhydrous forms A and B, the process their preparation by crystallization from acetone, as well as forms with bound water and their use as a medicament or for manufacturing a pharmaceutical composition for treating hypertension.

DETAILED DESCRIPTION OF INVENTION

A new process for the preparation of irbesartan is disclosed, which proceeds via irbesartan hydrohalide salt (2) as depicted below:

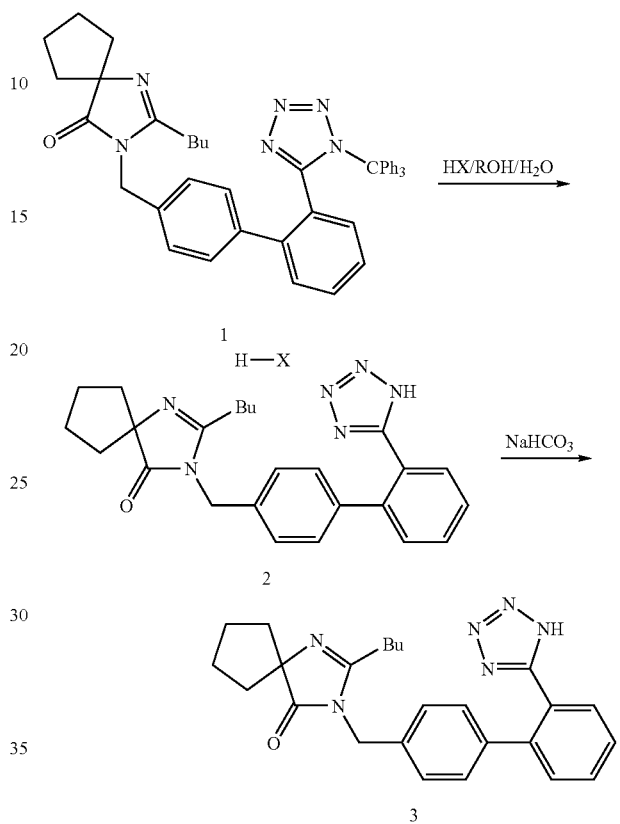

Protected derivative of irbesartan is 2-n-butyl-3-[[2'-(tetrazol-5-yl)biphenyl-4-yl]methyl]-1.3-diazaspiro[4.4]non-1-en-4-one carrying a protecting group on the tetrazole moiety, which may be any commonly used protecting group, for example alkyl or (poly)arylalkyl, such as t-t-butyl, or diphenylethyl. The specific protecting groups are selected from trityl, tert-butyl, cyclohexyl, sec-butyl, i-pentyl, i-propyl, diphenylmethyl, phenylmethyl, diphenylethyl, phenylethyl, diphenlypropyl. In particular case a trityl(triphenylmethyl) group of 2-butyl-3-[[2'-[1-(triphenylmethyl)-1H-tetrazol-5-yl][1,1'-biphenyl]-4-yl]methyl]-1,3-diazaspiro[4.4]non-1-en-4-one (1) (Trityl irbesartan) is removed in the presence of hydrohalic acid, in the mixture of water miscible organic solvent and water. Thus prepared hydrohalide salt of irbesartan (2) is isolated and recrystallized from appropriate solvent, preferably acetone, and is subsequently dissolved in (preferably hot) mixture of water miscible organic solvent (preferably ethanol) and water and neutralized with inorganic base to convert it to irbesartan and isolated by extraction or filtration. Optionally the product is crystallized, preferably from ethanol, to ensure irbesartan (3) with purity greater than 99.7%.

The first isolated hydrohalide salt of irbesartan may comprise impurities present from the synthesis of protected irbesartan and in particular triphenylmethanole and may not be more pure than 85%.

In the process of converting protected irbesartan or irbesartan into hydrobromide various polymorphs are formed.

Among them forms A and B can be both formed from acetone, and are advantageous for the process of purification of irbesartan into acid addition salt and back into irbesartan because of the simple choice of solvent, as well as their crystallinity.

Figure 1:
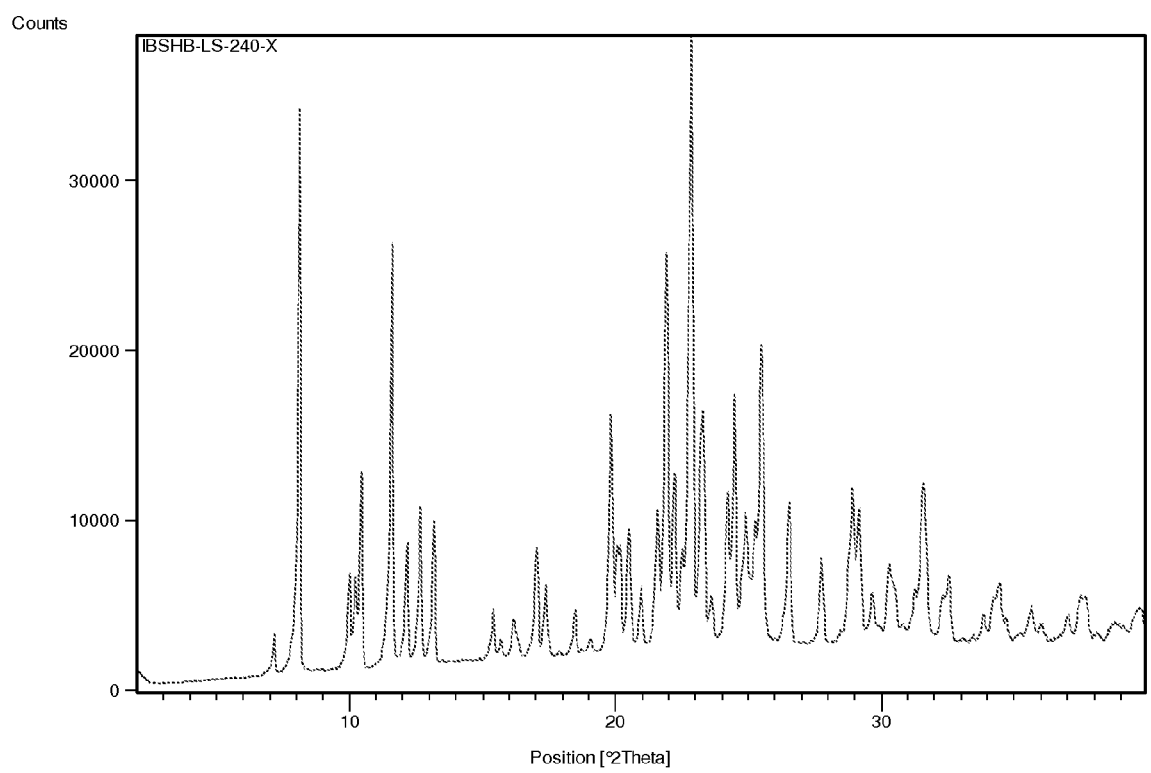
FIG. 1. X-ray powder diffractogram of anhydrous irbesartan hydrobromide form A.
Figure 2:
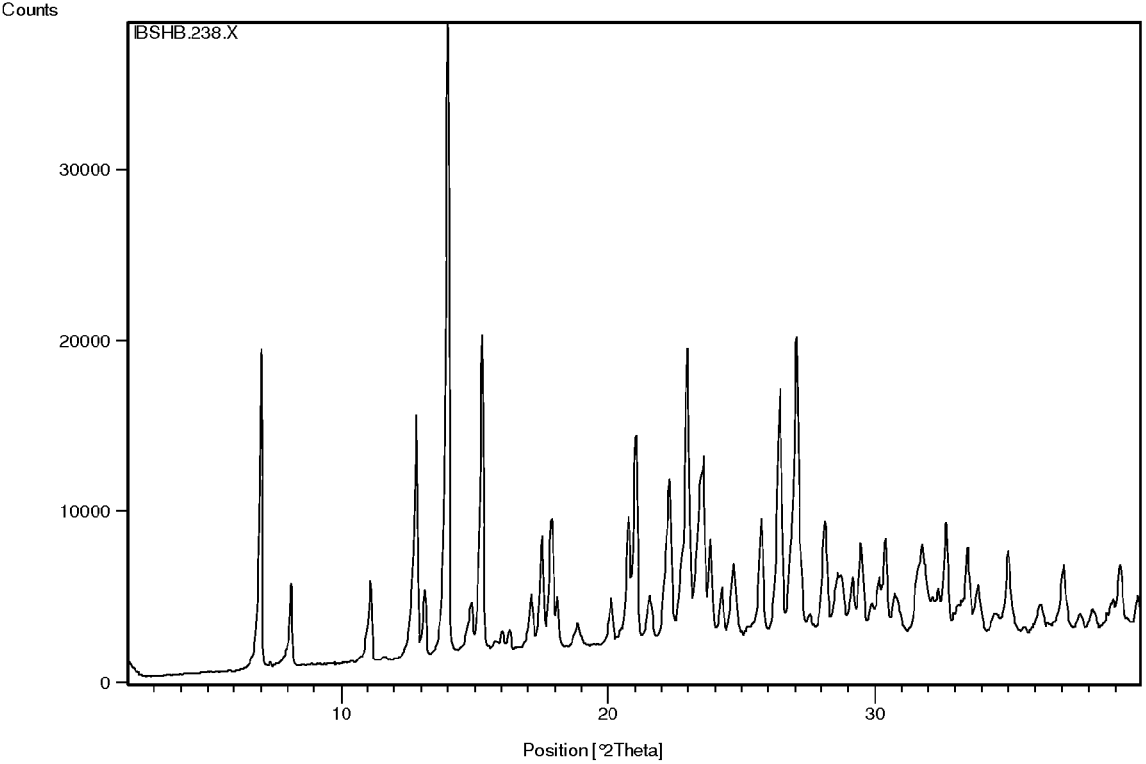
FIG. 2. X-ray powder diffractogram of anhydrous irbesartan hydrobromide form B.

Irbesartan hydrobromide form A is characterized by the diffractions in X-ray diffraction pattern substantially as in FIG. 1 at following 2-theta values: 7.2, 8.1, 11.6, 12.2, 12.7, 13.2, 19.8, 21.9, 22.9, 25.5° (in particular 8.1, 11.6, and 22.9±0.2°); IR spectra having characterizing peaks at 3425, 2964, 2715, 1775, 1628, 1516, 1476, 1328, 1069, 755 cm$^{-1}$; and melting point 196-199° C. Irbesartan hydrobromide form B is characterized by the diffractions in X-ray diffraction pattern substantially as in FIG. 2 at 2-theta values: 7.0, 11.1, 12.8, 14.0, 15.3, 23.0, 27.1° (in particular 7.0, 14.0, 23.0, and 27.1±0.20). Irbesartan hydrobromide form B is formed upon crystallization from less concentrated solution in acetone without stirring, in lower yield than form A.

Thus when dissolving irbesartan hydrobromide in boiling acetone at concentrations above 120 mg/ml form A crystallizes while from acetone at 25° C. and concentrations below 65 mg/ml crystallizes form B.

When purifying via hydrochloride salt a form characterized by the following 2-theta values: 8.4, 8.8, 10.2, 11.9, 16.5, 17.6, 20.4, IR spectra having absorptions at: 3433, 2959, 1770, 1628, 1515, 1475, 1352, 1047, 752 cm$^{-1}$ and m.p. 190-192° C. is formed.

Purification via this hydrochloride salt and hydrobromide salt form A is advantageous, because they begin to form already in boiling acetone solution and thus separate well from the impurities soluble in boiling acetone.

When dissolved in physiological medium, those salts behave similarly to irbesartan and are expected to exhibits comparable efficiency as antihypertensive, so they can be used for manufacturing a pharmaceutical composition; preferably for treating hypertension.

Raw irbesartan hydrobromide precipitates from water or aqueous solution, with bound up to 10% by weight water; as hydrate with amount of water around 3 molecules per 2 molecules of irbesartan which upon drying converts to a hydrate having approximately 1 mol of water per mol of irbesartan as determined by Karl Fischer method (monohydrate), and is upon crystallization from nonaqueous solvent (e.g, acetone converted) obtained in anhydrous crystalline forms. Irbesartan hydrobromide with bound water is less electrostatic than either form A or B and is thus (because of less undesired interactions with excipients and tableting equipment) easier to formulate into pharmaceutical composition, especially when high amount of irbesartan is desired in single tablet.

It has been surprisingly found that a further single recrystallization step or either irbesartan hydrochloride or hydrobromide in acetone gives a hydrohalide salt of irbesartan of purity exceeding 98.7% as determined by HPLC. The yield in respective step of formation of HCl salt is 84% and of HBr salt 87%, while the subsequent recrystallization yield is about 85%, giving a substance having a purity exceeding 98.7% in overall yield 72-74%.

The described process is clearly advantageous compared to simple deprotection of trityl irbesartan by a hydrohalic acid being added in amount sufficient for deprotection but insufficient for salt formation. Namely deprotection of a trityl irbesartan following the same procedure however only adding an acid until pH=2.5 or upon adding excess of an acid and thereafter neutralizing with an alkali until pH=7-7.5, upon subsequent concentration and precipitation from ethanol gives irbesartan in 30% yield and purity about 93.3%.

It has been found that in particular purification via HCl and HBr salts are feasible, especially when using a concentrated aqueous solution or a gas. Use of HBr is particularly advantageous, because it is less corrosive than HCl, and it is commercially available more concentrated.

Furthermore purification via HBr salt is advantageous in subsequent step where this salt is dissolved in hot mixture of solvents and extracted, not only because it is more stable against degradation (This may be due to higher melting point) but particularly because of technological and economical advantages due to better solubility of hydrobromide salt in boiling acetone as shown by following table:

|  | amount of acetone needed to dissolve 1 g | yield of crystallization upon cooling to room temp. |
| --- | --- | --- |
| irbesartan | 100 ml | 80% |
| irbesartan HCl | 15 ml | 84% |
| irbesartan HBr | 6 ml | 87% |

Furthermore, a robust purification technique allows the use of trityl irbesartan of purity as low as 75%, and still yields irbesartan of exceptional purity (above 99.8%). Based on this fact, the overall synthesis of irbesartan is thus considerably simplified, because additional purification of trityl irbesartan is not required, thus providing exceptionally pure irbesartan at reduced expenses.

The preferred purification process of our invention comprises following steps:

In the first step trityl irbesartan (1) is dissolved in the mixture of water miscible organic solvent and water, where organic solvent may be selected from lower alcohols, carboxylic acids, acetonitrile, acetone, dimethylsulphoxide, N,N-dimethylformamide, N,N-dimethylacetamide, 1,4-dioxane, THF, acetone or mixture thereof; preferably alcohols, more preferably methanol or ethanol; organic solvent and water can be mixed in any ratio where irbesartan hydro halide remains soluble, preferably two parts solvent one part water. To this solution is added hydrohalic acid HX, where X represents halide ion Cl, Br, I; preferably HBr, preferably as a concentrated aqueous solution, but can be added also as gas. Hydrohalic acid is added in ratio from 1 to 10, preferably 3 molar equivalents; preferably 3 fold excess. By this pH of reaction mixture should be between 0 and 3, more preferably to assure complete conversion between 0 and 2, and specifically below 2 (e.g. 0.5-1.9). Temperature at which reaction is performed should be in range from −80 to 160° C., preferably from 0 to 50° C.; more preferably from 20 to 35° C.

Reaction mixture is concentrated to completely or partially remove organic solvents, and resulting aqueous suspension is stirred at room temperature to achieve maximum yield, then filtered to collect irbesartan hydrohalide salt.

In the following step irbesartan hydro halide salt is recrystallized from suitable solvent such as acetone, THF, 2-methyl-THF, 1,4-dioxane, N,N-dimethylformamide, N,N-dimethylacetamide, methanol, ethanol, propanol, 2-propanol, preferably acetone.

In the subsequent step of the process irbesartan hydrohalide salt is dissolved in the mixture of water miscible organic solvent and water, where organic solvent is selected from lower alcohols, carboxylic acids, acetonitrile, acetone, dimethylsulphoxide, N,N-dimethylformamide, N,N-dimethylacetamide, 1,4-dioxane, THF, acetone or mixture thereof; preferably alcohols, more preferably methanol or ethanol; organic solvent and water can be mixed in any ratio where irbesartan hydro halide remains soluble, preferably two parts solvent to one part water; to this solution is added aqueous solution of inorganic base selected from carbonates, hydrogen carbonates, hydroxides, alkoxydes, preferably hydrogen carbonates, more preferably $NaHCO_3$. Depending on the concentration, either a suspension or solution of irbesartan is formed.

Upon optional concentration, solids may be filtered and recrystallized from ethanol to give irbesartan of purity greater than 99.7%.

In another embodiment of invention, suspension of irbesartan may be extracted with dichloromethane or other suitable solvent, organic phases are concentrated to give colorless syrup which is dissolved in boiling ethanol and left to crystallize to give irbesartan of purity greater than 99.7%.

In another embodiment of invention, dichloromethane or other suitable solvent may be added to solution of irbesartan hydro halide salt in abovementioned media. To this diphase system, vigorously stirred, solution of inorganic base is added. Phases are separated; organic phase is concentrated to give colorless syrup which is dissolved in boiling ethanol and left to crystallize to give irbesartan of purity greater than 99.7%.

The following examples are offered to illustrate aspects of the present invention, and are not intended to limit or define the present invention in any manner. The purity as used in this specification is determined by HPLC and is defined as ratio of area of irbesartan total area. In particular it can be determined if subjecting the mixture to a chromatography on C18 column and using water/acetonitrile and phosphate buffer (pH 2.5) as eluent. X-ray powder diffractograms were recorded with diffractometer X'Pert PRO MPD; CuKα radiation and it is understood that the intensity of the diffraction signals may vary as a function of particle size of the sample or orientation, and that diffractions recorded under different conditions, i.e. different difractometers may differ for as much as ±0.2° 2-theta, but preferably not more than ±0.1° 2-theta. To account for this variability one allows for error margins ±0.2° 2-theta when comparing diffraction patterns, however in that case majorly those characteristic peaks should be compared where error margins do not overlap. IR Spectra were recorded with Nicolet Nexus FT-IR melting points were established by Mettler Toledo DSC822.

EXAMPLE 1

To a solution of compound 1 (13.93 g) in the 240 ml mixture of ethanol/water (2:1), 4.6 ml of conc. (36%) HCl was added and stirred at r.t. for 3 hours. Suspension was filtered and filtrate concentrated in vacuo to remove ethanol. Concentrate was stirred at r.t. for 2 h, to form white precipitate which was collected by filtration and recrystallized from acetone. Crystalline product was dissolved in 120 ml mixture of ethanol/water (2:1), to which solution of 1.46 g $NaHCO_3$ in 70 ml water was added and stirred at r.t. for 60 min. Suspension was extracted with $CH_2Cl_2$ (3×150 ml), organic phases were collected and concentrated. Oily residue was dissolved in 60 ml of boiling ethanol, and then left to crystallize. Crystalline product was then filtered and dried to give 5.48 g of irbesartan (99.96 area %; assay: 99.8%).

EXAMPLE 2

To a solution of compound 1 (13.93 g) in the 240 ml mixture of ethanol/water (2:1), 7.0 ml of conc. (45%) HBr was added and stirred at r.t. for 3 hours. Suspension was filtered and filtrate concentrated in vacuo to remove ethanol. Concentrate was stirred at r.t. for 2 h, to form white precipitate which was collected by filtration and recrystallized from acetone. Crystalline product was dissolved in 120 ml mixture of hot ethanol/water (2:1) and 150 ml of $CH_2Cl_2$. Diphase system was stirred vigorously while heating to reflux temperature, then solution of 1.46 g $NaHCO_3$ in 70 ml water was added. Phases were separated, water solution was extracted with hot $CH_2Cl_2$ (2×150 ml), organic phases were collected and concentrated. Oily residue was dissolved in 60 ml of boiling ethanol, and then left to crystallize. Crystalline product was then filtered and dried to give 5.42 g of irbesartan (99.83 area %; assay: 99.7%).

EXAMPLE 3

To a solution of compound 1 (13.93 g) in the 240 ml mixture of ethanol/water (2:1), 4.6 ml of conc. (36%) HCl was added and stirred at r.t. for 3 hours. Suspension was filtered; filtrate was neutralized with $NaHCO_3$ until pH of suspension is 7-7.5. White precipitate was collected by filtration to give 1.35 g of irbesartan of bad quality (34 area %).

EXAMPLE 4

To a solution of compound 1 (13.93 g) in the 240 ml mixture of ethanol/water (2:1), 2.2 ml of conc. (36%) HCl was added and stirred at r.t. for 5 hours. Suspension was filtered; filtrate was neutralized with $NaHCO_3$ until pH of suspension is 7-7.5. Suspension was extracted twice with 150 ml $CH_2Cl_2$, organic phases were concentrated and crystallization was induced by addition of ethanol to give 2.83 g of irbesartan (93.3 area %).

EXAMPLE 5

Raw irbesartan hydrochloride (10.52 g, 89.26 area %) was dissolved in boiling acetone (160 ml) and continuously stirred in boiling acetone until fine white precipitate forms. After cooling to r.t., precipitate was collected by filtration to give 7.89 g of irbesartan hydrochloride (99.8 area %).

IR (Characteristic peaks): 3433, 2959, 1770, 1628, 1515, 1475, 1352, 1047, 752 $cm^{-1}$ m.p. 190-192° C.

EXAMPLE 6

Raw irbesartan hydrobromide (11.88 g, 88.42 area %) was dissolved in boiling acetone (80 ml) and continuously stirred in boiling acetone until fine white precipitate forms. After cooling to r.t., precipitate was collected by filtration to give 9.08 g of irbesartan hydrobromide form A (98.8 area %).

IR (Characteristic peaks): 3425, 2964, 2715, 1775, 1628, 1516, 1476, 1328, 1069, 755 $cm^{-1}$ m.p. 196-199° C.

EXAMPLE 7

Raw irbesartan hydrobromide (12.86 g, 89.32 area %) was dissolved in boiling acetone (200 ml) and instantaneously left to cool to r.t without stirring. After cooling to r.t., precipitate was collected by filtration to give 8.57 g of irbesartan hydrobromide form B (98.8 area %).

The invention claimed is:
1. A crystalline hydrobromide acid addition salt of 2-n-butyl-3-[[2'-(tetrazol-5-yl)biphenyl-4-yl]methyl]-1.3-diazaspiro[4.4]non-1-en-4-one having an X-ray diffraction pattern at the following 2-theta values: 8.1, 11.6, and 22.9±0.2° or
characterized by X-ray diffraction pattern as presented in FIG. 1,
or characterized by diffractions in X-ray diffraction pattern at the following 2-theta values: 7.2, 8.1, 11.6, 12.2, 12.7, 13.2, 19.8, 21.9, and 22.9±0.1°.

2. The crystalline hydrobromide acid addition salt of 2-n-butyl-3-[[2'-(tetrazol-5-yl)biphenyl-4-yl]methyl]-1.3-diazaspiro[4.4]non-1-en-4-one according to claim 1 having IR spectra having characterizing peaks at 3425, 2964, 2715, 1775, 1628, 1516, 1476, 1328, 1069, and 755 cm$^{-1}$; and a melting point from 196-199° C.

3. A crystalline hydrobromide acid addition salt of 2-n-butyl-3-[[2'-(tetrazol-5-yl)biphenyl-4-yl]methyl]-1.3-diazaspiro[4.4]non-1-en-4-one having an X-ray diffraction pattern at the following 2-theta values: 7.0, 14.0, 23.0, and 27.1±0.2°.

4. The crystalline hydrobromide acid according to claim 3 characterized by diffractions in X-ray diffraction pattern at following 2-theta values: 7.0, 11.1, 12.8, 14.0, 15.3, 23.0, and 27.1±0.1°.

5. A process comprising the following steps:
 a) converting protected irbesartan into a hydrohalide salt of irbesartan;
 b) isolating said hydrohalide salt of irbesartan; and
 c) converting said isolated hydrohalide salt of irbesartan into irbesartan,
 wherein the hydrohalide salt is a crystalline hydrobromide acid addition salt according to claim 1 or 3.

6. A process for the manufacturing of pure irbesartan comprising converting irbesartan or a protected derivative thereof into an isolated hydrohalide acid addition salt, whereupon said hydrohalide acid addition salt is converted into irbesartan, and wherein the hydrohalide salt is a crystalline hydrobromide acid addition salt according to claim 1 or 3.

7. The process according to claim 6, wherein the protected irbesartan is 2-n-butyl-3-[[2'-(tetrazol-5-yl)biphenyl-4-yl]methyl]-1.3-diazaspiro[4.4]non-1-en-4-one, carrying the protecting group on tetrazol.

8. The process according to claim 7, wherein the protecting group on tetrazol is either an alkyl or an alkyl substituted by one or more aryls.

9. The process according to claim 7, wherein the protecting group on tetrazol is selected from trityl, tert-butyl, cyclohexyl, sec-butyl, i-pentyl, propyl, diphenylmethyl, phenylmethyl, diphenylethyl, phenylethyl and diphenlypropyl.

10. A process for synthesis of 2-n-butyl-3-[[2'-(tetrazol-5-yl)biphenyl-4-yl]methyl]-1.3-diazaspiro[4.4]non-1-en-4-one that comprises the following steps:
 a) providing a solution or suspension of 2-n-butyl-3-[[2'-(trityl tetrazol-5-yl)biphenyl-4-yl]methyl]-1.3-diazaspiro[4.4]non-1-en-4-one in a mixture of an organic solvent miscible with water and water;
 b) adding hydrobromide thereto until the pH is between 0 and 3;
 c) isolating 2-n-butyl-3-[[2'-(tetrazol-5-yl)biphenyl-4-yl]methyl]-1.3-diazaspiro[4.4]non-1-en-4-one hydrobromide in solid form to form the crystalline hydrobromide acid addition salt according to claim 1 or 3;
 d) recrystallizing said 2-n-butyl-3-[[2'-(tetrazol-5-yl)biphenyl-4-yl]methyl]-1.3-diazaspiro[4.4]non-1-en-4-one hydrobromide
 e) dissolving obtained 2-n-butyl-3-[[2'-(tetrazol-5-yl)biphenyl-4-yl]methyl]-1.3-diazaspiro[4.4]non-1-en-4-one hydrobromide in a mixture of an organic solvent miscible with water and water;
 f) adding an aqueous solution of a base thereto; and
 g) isolating 2-n-butyl-3-[[2'-(tetrazol-5-yl)biphenyl-4-yl]methyl]-1.3-diazaspiro[4.4]non-1-en-4-one in solid form; or
 h) extracting 2-n-butyl-3-[[2'-(tetrazol-5-yl)biphenyl-4-yl]methyl]-1.3-diazaspiro[4.4]non-1-en-4-one with a solvent nonmiscible with water; and
 i) isolating 2-n-butyl-3-[[2°-(tetrazol-5-yl)biphenyl-4-yl]methyl]-1.3-diazaspiro[4.4]non-1-en-4-one in solid form by removal of solvent or addition of an antisolvent which mixes with said solvent nonmiscible with water wherein step d) is optional.

11. The process according to claim 10, wherein in step b) is added until the pH is between 0 and 2.

12. The process according to claim 11, wherein in step b) hydrobromide is added until the pH is between 0.5 and 1.9.

13. The process according to claim 10, wherein the solvent nonmiscible with water is selected from the group consisting of $CH_2Cl_2$, $CCl_4$ and $CHCl_3$
 and/or
 wherein the organic solvent miscible with water is selected from the group consisting of alcohols, carboxylic acids, acetonitrile, acetone, dimethylsulphoxide, N,N-dimethylformamide, N,N-dimethylacetamide, 1,4-dioxane, THF and acetone.

14. The process according to claim 10, wherein the base is selected from the group consisting of carbonates, hydrogen carbonates, hydroxides and alkoxides.

15. The process according to claim 13, wherein the solvent nonmiscible with water is methylene chloride.

16. The process according to claim 13, wherein the organic solvent miscible with water is selected from C1-C5 alcohols.

17. The process according to claim 14, wherein the base is selected from hydrogen carbonates.

18. A process for converting 2-n-butyl-3-[[2'-(tetrazol-5-yl)biphenyl-4-yl]methyl]-1.3-diazaspiro[4.4]non-1-en-4-one hydrobromide, having purity below 90% as measured by HPLC, into 2-n-butyl-3-[[2'-(tetrazol-5-yl)biphenyl-4-yl]methyl]-1.3-diazaspiro[4.4]non-1-en-4-one having purity above 99% as measured by HPLC, the method comprising the steps of:
 a) crystallizing 2-n-butyl-3-[[2'-(tetrazol-5-yl)biphenyl-4-yl]methyl]-1.3-diazaspiro[4.4]non-1-en-4-one hydrobromide from acetone to form the crystalline hydrobromide acid addition salt according to claim 1 or 3;
 b) dissolving said 2-n-butyl-3-[[2'-(tetrazol-5-yl)biphenyl-4-yl]methyl]-1.3-diazaspiro[4.4]non-1-en-4-one hydrobromide in a mixture of an alcohol and water wherein the ratio of alcohol to water is between 3 and 1;
 c) adding an aqueous solution of an organic or inorganic base thereto in amount sufficient to yield 2-n-butyl-3-[[2'-(tetrazol-5-yl)biphenyl-4-yl]methyl]-1.3-diazaspiro[4.4]non-1-en-4-one;
 d) extracting 2-n-butyl-3-[[2'-(tetrazol-5-yl)biphenyl-4-yl]methyl]-1.3-diazaspiro[4.4]non-1-en-4-one with solvent nonmiscible with water; and
 e) isolating 2-n-butyl-3-[[2'-(tetrazol-5-yl)biphenyl-4-yl]methyl]-1.3-diazaspiro[4.4]non-1-en-4-one in solid form by removal of solvent or addition of an antisolvent which mixes with said solvent nonmiscible with water.

19. The process according to claim 18, wherein the solvent nonmiscible with water is selected from the group consisting of $CH_2Cl_2$, $CCl_4$ and $CHCl_3$
 and/or
 wherein the antisolvent is selected from the group consisting of alcohols, carboxylic acids, acetonitrile, acetone, dimethylsulphoxide, N,N-dimethylformamide, N,N-dimethylacetamide, 1,4-dioxane, THF and acetone.

20. The process according to claim 18, wherein the organic or inorganic base is selected from carbonates, hydrogen carbonates, hydroxides and alkoxides.

21. A process for manufacturing the crystalline hydrobromide acid addition salt of 2-n-butyl-3-[[2'-(tetrazol-5-yl)biphenyl-4-yl]methyl]-1.3-diazaspiro[4.4]non-1-en-4-one according to claim 1 or 3, containing from 0 to 10% by weight of water, comprising precipitating the hydrobromide acid addition salt from aqueous acetone.

22. A process for manufacturing the crystalline hydrobromide acid addition salt of 2-n-butyl-3-[[2'-(tetrazol-5-yl)biphenyl-4-yl]methyl]-1.3-diazaspiro[4.4]non-1-en-4-one according to claim 1 or 3, comprising crystallizing the hydrobromide acid addition salt from a solvent selected from the group consisting of acetone, THF, 2-methyl-THF, 1,4-dioxane, N,N-dimethylformamide, N,N-dimethylacetamide, methanol, ethanol, propanol, 2-propanol, and mixture thereof.

23. The process according to claim 22, wherein the crystallization is performed in acetone.

24. The process according to claim 23, wherein the crystallization is performed by providing a solution of irbesartan in acetone at a concentration above 120 mg/ml.

25. The process according to claim 22, wherein the crystallization is performed in acetone at room temperature.

* * * * *